United States Patent [19]

Evers

[11] Patent Number: 5,576,504
[45] Date of Patent: Nov. 19, 1996

[54] CONTAINER IDENTIFICATION APPARATUS

[75] Inventor: Timothy P. Evers, Wilmington, Del.

[73] Assignee: Dade Chemistry Systems Inc., Deerfield, Ill.

[21] Appl. No.: 516,593

[22] Filed: Aug. 18, 1995

Related U.S. Application Data

[62] Division of Ser. No. 276,187, Jul. 15, 1994, Pat. No. 5,517,867.

[51] Int. Cl.$^6$ ................................................. G01M 19/00
[52] U.S. Cl. ........................................ 73/865.9; 250/576
[58] Field of Search ......................... 73/863.85, 864.24, 73/864.25, 865.9; 141/329, 330; 206/459.1; 250/576, 223 B; 356/246

[56] References Cited

U.S. PATENT DOCUMENTS

| | | | |
|---|---|---|---|
| 3,203,248 | 8/1965 | Stutler et al. | 73/863.85 |
| 3,503,265 | 3/1970 | Isreeli | 73/864.24 X |
| 3,748,911 | 7/1973 | Rousselet et al. | 73/864.25 X |
| 3,991,627 | 11/1976 | Laird et al. | |
| 4,120,662 | 10/1978 | Fosslien | 422/63 X |
| 4,274,453 | 6/1981 | Lee | 141/1 |
| 4,342,341 | 8/1982 | Lee | 141/330 X |
| 4,475,411 | 10/1984 | Wellerfors | 73/864.24 |
| 4,478,095 | 10/1984 | Bradley et al. | 73/864.21 |
| 4,570,495 | 2/1986 | Terada | 73/864.25 |
| 4,577,514 | 3/1986 | Bradley et al. | 73/863.01 |
| 4,713,974 | 12/1987 | Stone | 73/864.23 |
| 4,721,137 | 1/1988 | Muller | 141/65 |
| 4,756,201 | 7/1988 | Uffenheimer | 73/864.83 |
| 4,836,038 | 6/1989 | Baldwyn | 73/864.25 X |
| 4,951,512 | 8/1990 | Mazza et al. | 73/861.23 |
| 4,962,041 | 10/1990 | Roginski | 436/150 |
| 4,977,786 | 12/1990 | Davis | 73/864.24 X |
| 5,080,864 | 1/1992 | Shaw | 422/62 |
| 5,132,088 | 7/1992 | Waketake | 73/864.24 X |
| 5,201,232 | 4/1993 | Uffenheimer | 73/864.23 |
| 5,216,926 | 6/1993 | Lipscomb | 73/864.25 |
| 5,270,211 | 12/1993 | Kelln et al. | 436/43 |
| 5,285,823 | 2/1994 | Honda | 73/863.85 X |
| 5,306,510 | 4/1994 | Meltzer | 73/864.24 X |
| 5,417,123 | 5/1995 | D'Autry | 73/864.25 |
| 5,445,037 | 8/1995 | Itoh | 73/864.25 |

FOREIGN PATENT DOCUMENTS

| | | |
|---|---|---|
| 0223758 | 5/1987 | European Pat. Off. |
| WO92/08988 | 5/1992 | WIPO |

Primary Examiner—Thomas P. Noland

[57] ABSTRACT

An apparatus is provided for identifying each of a predetermined plurality of liquid containers, some of which are stoppered and others of which are open-mouthed and for extracting liquid therefrom. The apparatus comprises an upper arm and a lower arm and a sensor responsive to relative motion therebetween, relative motion between the arms causing a container identity signal representative to be generated. A single needle is used to penetrate stoppers when present and extract liquid from the container.

7 Claims, 4 Drawing Sheets

CONTAINER IDENTIFICATION APPARATUS

CROSS REFERENCE TO RELATED APPLICATION

This is a division of application Ser. No. 08/276,187, filed Jul. 15, 1994, now U.S. Pat. No. 5,517,867.

Application Ser. No. 08/276,186 (IP-0970), now abandoned in favor of continuation application Ser. No. 08/592,774, Jan. 26, 1996 (IP-970-A), filed contemporaneously herewith in the names of Bernstine et al. and assigned to the assinee of the present application, discloses and claims an analysis instrument with which the present invention may be used.

BACKGROUND OF THE INVENTION

1. Field of the Invention

The present invention relates to a liquid extraction apparatus, and in particular, to an apparatus for extracting a liquid from any one of a plurality of liquid containers, whether the container has an open mouth or a stoppered mouth.

2. Description of the Prior Art

In the field of automatic analysis instruments a premium is placed on the ability of an instrument to process a relatively large number of different liquid samples without operator intervention. Liquids which are non-toxic and non-hazardous in nature are carried in open containers, such as open test tubes. However, to avoid exposing operators to contact with a potentially hazardous material, any unsafe liquid material is carried in a closed container, i.e., a container whose mouth is closed by a rubber stopper or other suitable cap mechanism. Exemplary of a suitable closed container is that container sold by Becton-Dickinson Company, East Rutherford, N.J., under the trademark Vacutainer®. Such a container is evacuated to facilitate aspiration of a whole blood sample.

Complications are encountered with the use of an evacuated closed container. One complication is the need of a relatively more substantial extraction needle to penetrate the rubber stopper. A further complication is the difficulty in extracting accurately a predetermined volume of liquid due to air pressure within the tube. This problem has been addressed by using an outer penetrating needle to puncture the stopper and equalize air pressures followed by the insertion of an inner liquid extraction needle to aspirate liquid.

In addition to being able to aspirate liquid sample from both open and stoppered containers, to effectuate versatility in handling sample containers from a variety of sources it is important that a sample probe apparatus be able to automatically identify and accomodate containers having different physical characteristics, in particular, containers that are stoppered or open-mouthed or that have different heights and diameters.

In view of the foregoing, it is believed advantageous to provide a liquid extraction apparatus having the ability to identify the type of sample container from which a liquid sample is to be extracted. Moreover, it is also believed advantageous to provide a liquid extraction apparatus having such flexibility of operation as to extract liquid samples from either stoppered or open containers using a single needle.

U.S. Pat. No. 3,991,627 (Laird et al.) discloses a device for aligning sample containers (within some predetermined range of sizes) regardless of the container's size. The device has an outer piercing needle that passes throught the septum of a container and an inner needle movable within the piercing needle. Liquid is aspirated from the container through the inner needle.

U.S. Pat. No. 4,951,512 (Mazza et al) discloses a liquid extraction apparatus employing an outer puncture tube to form a temporary opening in a stopper of a sample liquid container and an inner extraction needle to remove an amount of liquid from the container. A lift assembly moves a sample container upward against the puncture tube. After liquid is extracted a stripper assembly strips the container from the puncture tube, allowing the opening to close.

Other devices that employ an outer puncturing tube and an inner liquid extraction needle include U.S. Pat. Nos. 4,478,095 and 4,577,514 (both to Bradley et al.) and U.S. Pat. No. 4,721,137 (Mueller).

U.S. Pat. Nos. 4,756,201 and 5,201,232 (both to Uffenheimer) both disclose an apparatus that extracts liquid from open and closed containers. These apparatus both additionally require that a closed tube be segregated by an operator and positioned upside-down for extraction to occur.

U.S. Pat. No. 5,270,211 (Kelln) accomodates sample containers of different heights using an elevationally movable arm carrying a receptacle for receiving the containers. A spring-biased tube clamp urges each container against rib guides within the receptacle to transversely center containers of differing diameters. A puncture tube is used to puncture resealably a conventional closure on a container and a pipette is positioned within the puncture tube to extract sample liquid from the container. A bifurcated stripper engages the upper surface of a container to prevent upward movement of the container during removal of the puncture tube.

U.S. Pat. No. 5,080,864 (Shaw) discloses a stopper detector using a rotating flag-like mechanism for use in conjunction with a stopper remover.

U.S. Pat. No. 4,962,041 (Roginski) provides a single extracting needle that is lowered to puncture a stopper closing a liquid container and withdraw a sample liquid. A retainer having a latching mechanism prevents the withdrawal or loosening of the stopper due to friction generated during the withdrawal of the needle from the stopper.

SUMMARY OF THE INVENTION

In a first aspect the present invention is directed toward an apparatus for identifying each of a predetermined plurality of liquid containers, some of which are stoppered and others of which are open-mouthed. The apparatus comprises an upper arm and a lower arm, with the lower arm being mounted for relative movement along a vertically oriented penetration axis with respect to the upper arm. An actuator is connected to the upper arm for rectilinearly displacing the same. A sensor responsive to relative motion between the upper and the lower arms generates a first signal that is applied to means responsive thereto for generating a signal representative of the magnitude of the displacement of the upper arm. Means, such as a memory device, responds to the magnitude of the displacement signal to generate a container identity signal. The upper and the lower arms are initially displaceable as a unit by the actuator until abutting contact between the lower arm and a container to be identified prevents further advance of the lower arm. Simultaneously, relative motion between the upper and the lower arms causes the sensor to generate the first signal.

The memory has a plurality of storage locations therein, with each storage location containing a container identity signal representative of the identity of one of the plurality of containers. Each storage location has an address that corresponds to a different magnitude of displacement signal.

The sensor arrangement preferably includes a light emitting element and a light receiving element disposed on the upper arm in proximity to the opening therein. A tab extending from the alignment post is disposed between the light emitting element and the light receiving element while the upper and lower arms are moved as unit. However, relative motion of the lower arm with respect to the upper arm displaces the tab from between the light emitting element and the light receiving element, thereby to generate the first signal.

In the preferred form of construction the upper arm has an opening therethrough while the lower arm has an alignment post secured thereto. The alignment post extends from the lower arm and through the opening in the upper arm. A foot may be attached to the lower arm. The foot has a surface that is inclined with respect to the penetration axis. The inclined surface of the foot is that portion of the lower arm which makes abutting contact with the container to be identified. In the preferred implementation, the bottom end of each container is supported at the same predetermined reference datum.

In another aspect the present invention is directed to an apparatus for extracting a liquid from either an open-mouthed or a stoppered liquid container. The upper arm carries a single extraction needle at a first lateral end thereof. The needle depends from the upper arm in alignment with the penetration axis. In this aspect of the invention the foot attached to the lower arm has a conically shaped surface therein and a central axial bore therethrough. The bore opens onto the conical shaped surface and is aligned vertically with the penetration axis. The lower end of the extraction needle is initially disposed within the bore. The upper and the lower arms move as a unit until, in a manner as described above, the conically shaped surface on the foot abuts the upper end of a container. This abutting action between the conical surface on the lower arm and the container draws the container into and secures the container in an operating position in which the axis of the container is collinear with the penetration axis. Continued displacement of the upper arm by the actuator with respect to the lower arm extends the extraction needle from the bore and causes the needle to penetrate through the stopper if present without buckling of the extraction needle and to enter into the container.

In the preferred form a pair of vertically extending plates is attached to the lower arm. The combination of the plates and the lower arm has sufficient weight to generate a holding force that retains the container in the operating position when the acutator displaces the upper arm in the second direction to withdraw the extraction needle through the stopper if present and from the container.

BRIEF DESCRIPTION OF THE DRAWINGS

The present invention will be fully understood from following detailed description thereof, taken in connection with the accompanying drawings, which form a part of this application, and in which.

DETAILED DESCRIPTION OF THE INVENTION

Figure 1:
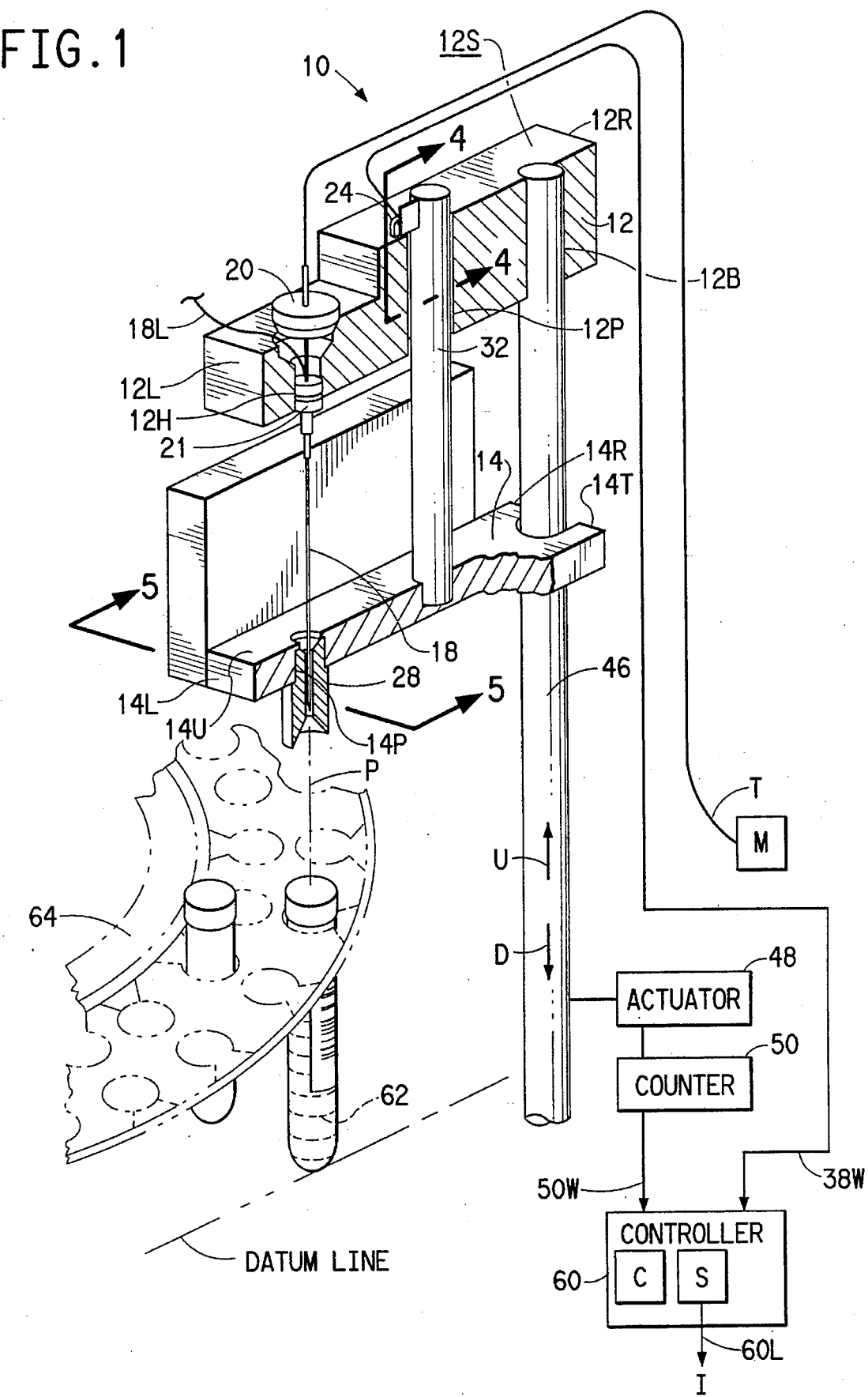
FIGS. 1 through 3 are side elevational views, each in perspective and each having cut away portions shown in section, illustrating the construction of a liquid extraction apparatus in accordance with the present invention, with various functional elements of the apparatus being illustrated in schematic form.

Throughout the following detailed description, similar reference numerals refer to similar elements in all Figures of the drawings.

Figure 2:
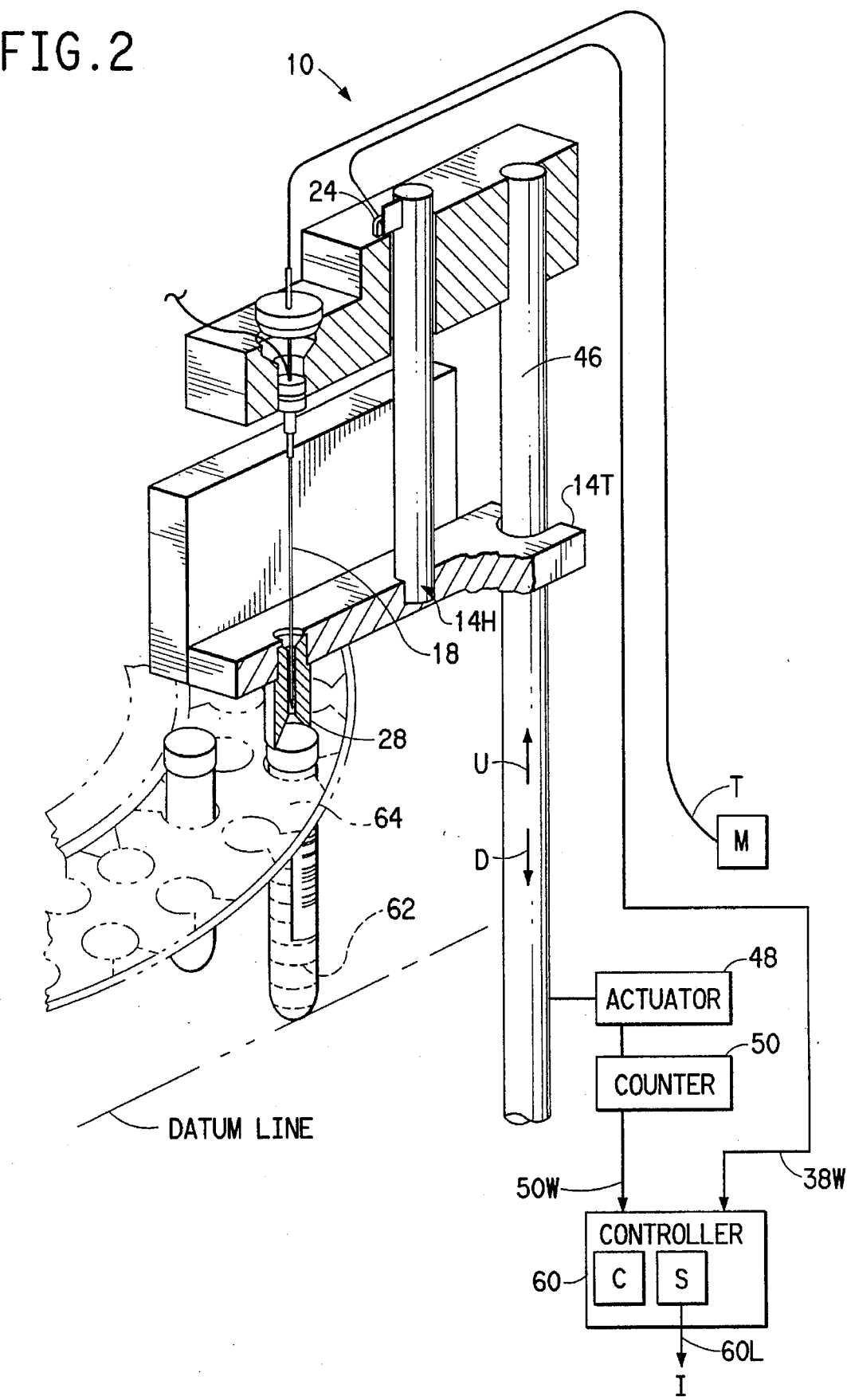
Figure 3:
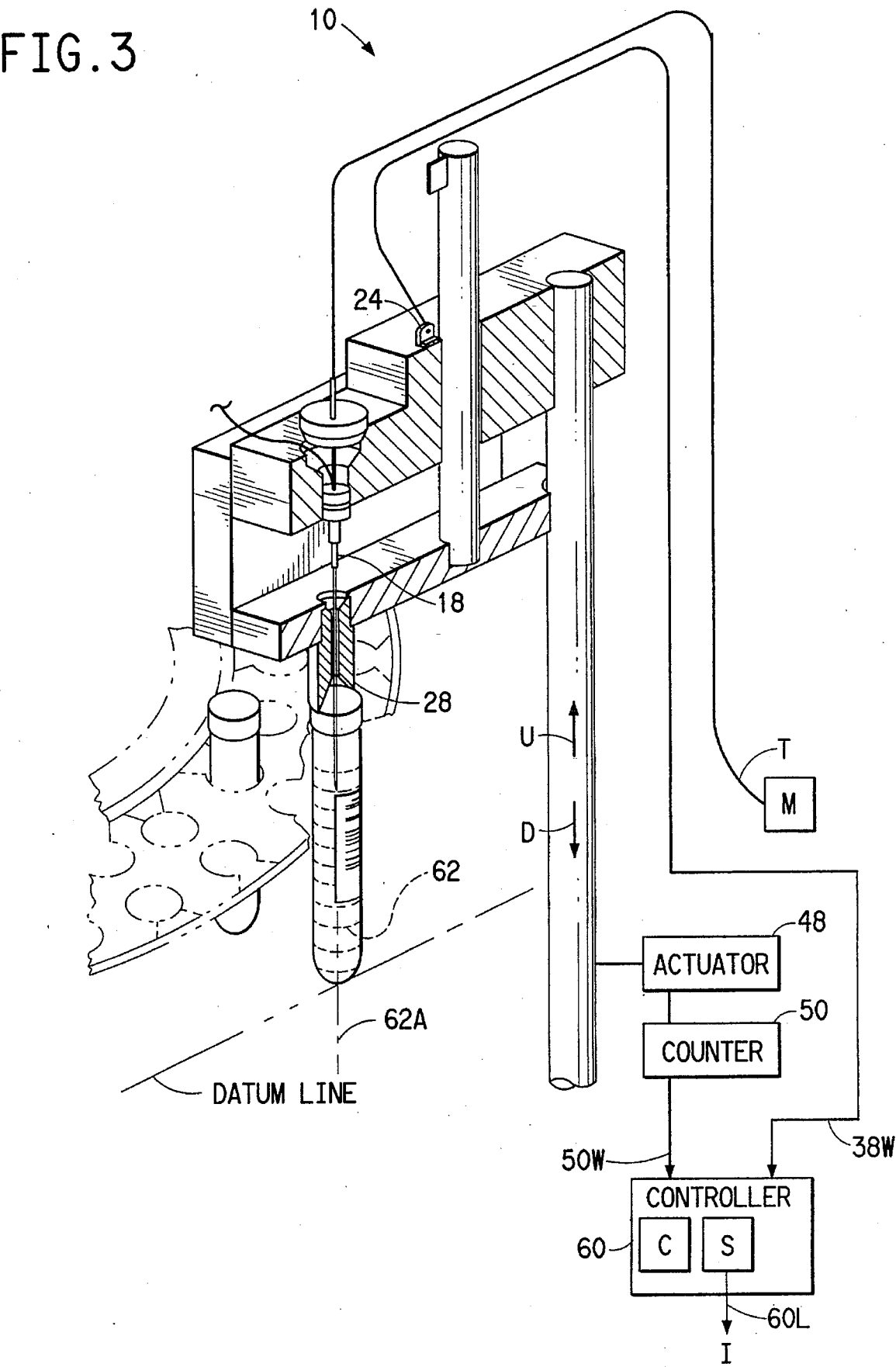

FIGS. 1 through 3 are side elevational perspective views of a liquid extraction apparatus generally indicated by the reference character 10 in accordance with the present invention. The apparatus 10 includes an upper arm 12 and a lower arm 14. As will be developed the upper arm 12 and the lower arm 14 are mounted for relative movement with respect to each other along a vertically oriented penetration axis P.

The upper arm 12 is a beam-like member, preferably fabricated from aluminum. The arm 12 has an upper planar surface 12S, a first lateral end 12L and a second lateral end 12R. The basic thickness dimension of the arm 12 is reduced near the first end 12L thereof. The arm 12 has a bore 12B provided therethrough adjacent the second end 12R. The upper arm 12 has an opening 12P therethrough, the opening 12P being located substantially midway between the first end 12L and second end 12R.

A single extraction needle 18 having with a lower end thereon depends from the first end 12L of the upper arm 12. The needle 18 is oriented in aligned relationship with the penetration axis P. Preferably, the needle 18 is fabricated from Series 316, stainless steel, eighteen gauge, heavy wall, smooth bore tubing and has a free length on the order of four inches. The lower end of the needle 18 has a deflected point (visible in FIG. 5) that eliminates coring when the needle 18 passes through a stopper. Although a needle having such dimensions as set forth above might normally be expected to buckle upon penetration of an elastomeric stopper, utilization of the liquid extraction apparatus 10 in accordance with the present invention prevents such an occurrence.

The extraction needle 18 is secured to the arm 12, preferably using a threaded knob 21. The knob 21 is threadedly received in a threaded bore 12H adjacent to the end 12L of the arm 12. In the preferred case the knob 21 is fabricated from a polymeric material. The knob 21 totally surround a disc (not shown) that is secured (as by brazing) to the needle 18. The needle 18 passes through an insulating liner 20, also made from polymeric material, to preclude electrical contact between the needle 18 and the arm 12.

The needle 18 forms a part of a liquid level sensing arrangement. To this end a signal line 18L connects the needle 18 to a capacitive sensor C. Suitable for use as the capacitive sensor C is that arrangement disclosed in U.S. Pat. No. 4,977,786, issued Dec. 18, 1990 and assigned to the assignee of the present invention. In addition, a length of tubing T is connected from the uppermost end of the needle 18 to a pump M. Suitable for use as the pump M is that pump disclosed in *Research Disclosure,* March 1994, page 129.

The lower arm 14 is also a beam-like member fabricated from stainless steel. The arm 14 has an upper surface 14U and a lower planar surface 14S, a first lateral end 14L and a second lateral end 14R. The lower arm 14 has a through opening 14P adjacent to the first end 14L thereof. The second end 14R of the lower arm 14 is forked to define a pair of extending tines 14T.

Figure 5:
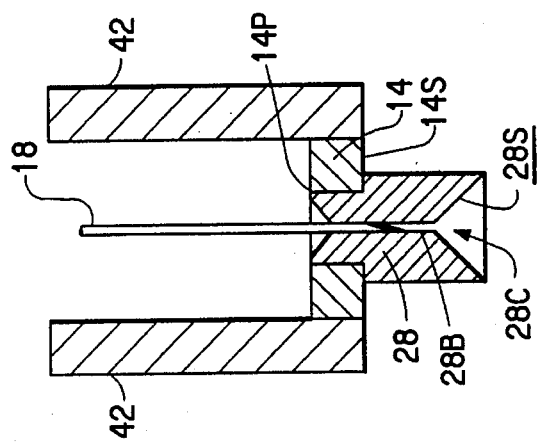
FIG. 5 is a side elevational view taken along view lines 5—5 in FIG. 1, illustrating another a portion of the apparatus in accordance with the present invention; and, FIG. 6 is a schematic illustration of a calibration process for a liquid extraction apparatus in accordance with the present invention.

As best seen in FIG. 5 foot 28 is attached within the opening 14P in the lower arm 14. The foot 28 is a generally cylindrical, barrel-like element that extends from the lower surface 14S of the lower arm 14. The lower end of the foot 28 has a generally conically shaped surface 28S that is inclined with respect to the vertical penetration axis P. The surface 28S defines a tapered cavity 28C. A bore 28B extends centrally and axially through the foot 28. The bore 28B opens onto the conical shaped surface 28S. The axis of the bore 28B is aligned vertically with the penetration axis P.

The lower arm 14 has a counterbored hole 14H that opens onto the upper surface 14U. An alignment post 32 is secured, as for example by a screw, within the hole 14H. The alignment post 32 extends upwardly from the lower arm 14 and passes freely through the opening 12P in the upper arm.

Figure 4:
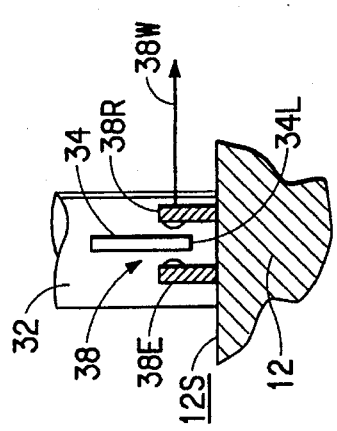
FIG. 4 is an elevational view of a portion of the apparatus of FIG. 1 taken along view lines 4—4 thereof.

As is best seen in FIG. 4 the uppermost portion of the alignment post 32 has an opaque, flag-like tab 34 extending radially outwardly therefrom. The lower horizontal edge of the tab 34 is indicated by the reference chracter 34L. For a reason that will become clearer herein the length of the radially extending tab is sufficient to interpose the tab 34 between a light emitting element 38E and a light receiving element 38R. The elements 38E, 38R are disposed on the upper surface 12S of the upper arm 12 in proximity to the through opening 12P. The elements 38E, 38R, in cooperatation with the tab 34, define a relative motion sensor 38 for a purpose to be described. The output signal from the sensor 38 is carried to a suitable system controller 60 on a line 38W.

A pair of vertically extending plates 42 is attached at the edges of the lower arm 14, one of the walls being omitted from the Figures for clarity. The plates 42 are fabricated of a relatively massive material. Series 300 stainless steel is preferred.

The apparatus 10 further includes an operating rod 46 that is securely attached, as by a press fit, into the bore 12B in the upper arm 12. The tines 14T extending from the second end 14R of the lower arm 14 bracket the operating rod 46 for the purpose of guiding the lower arm 14 therealong. The rod 46 has a vertical lead screw (not shown) disposed adjacent the opposite end thereof whereat the rod 46 is connected to an actuator 48.

As will be developed, the actuator 48 is operative to reversibly rectilinearly displace the upper arm 14 in opposed first and second directions as indicated by the arrow D, U, respectively. The actuator 48 is preferably implemented using a stepper motor with a step counter 50. For a purpose that will become more clear herein, the step counter 50 generates a signal on a line 50W representative of the magnitude of the displacement of the upper arm 14 along the vertically oriented penetration axis P. The signal from the device 50 is carried to system controller 60 along line 50W.

As will be further explained hereinafter, in addition to being able to extract a liquid carried within a container presented thereto, the liquid extraction apparatus 10 in accordance with the present invention also exhibits the capability of identifying each of a predetermined plurality of liquid containers, some of which are stoppered and others of which are open-mouthed. Such a capability proves important in the event that the extraction apparatus is used in connection with an analysis instrument as disclosed and claimed in the above referenced contemporaneously filed copending application, assigned to the assignee of the present invention. To this end the system controller 60 is operative to generate a container identity signal I. The container identity signal I serves to identify whether a given container presented to the apparatus 10 is stoppered or open-mouthed.

The apparatus hereinbefore described includes a sensor 38 that is responsive to relative motion between the upper arm 12 and the lower arm 14 to generate a first signal (on the line 38W), representative of the occurrence of relative motion between the arms 12, 14. In addition first means is provided that respond to the first signal for generating a second signal (on the line 50W) representative of the magnitude of the displacement of the upper arm 12 with respect to the penetration axis P. Further, second means responsive to the second signal (the magnitude of the displacement signal) generate a container identity signal I on a line 60L. The first and second means are preferably implemented using a microprocessor-based computer assisted system controller 60 configured to include a memory S. The memory S has a plurality of storage locations therein. Each storage location contains a container identity signal I representative of the condition (i.e., stoppered or open-mouthed) of one of a plurality of containers. Each storage location has an address that corresponds to the second signal (the magnitude of the displacement signal).

The operation of the liquid extraction apparatus in accordance with the present invention will become clear from the following description of the operation thereof.

The operation of the liquid extraction apparatus 10 will be explained in the context of a identifying and extracting liquid from one of a plurality of liquid containers 62 supported by container support 64. Each of the containers 62 is supported by the container support 64 such that the bottom end of each container 62 lies at the same common reference datum line. In the instance of short tubes, such as pediatric tubes, a spacer may optionally be used to extend the bottom of the tube to the common refernce datum line. The containers 62 may be manually or automatically placed in the support 64. Each container 62 contains liquid to be extracted and is in either an open-mouthed condition or stoppered condition and of different heights and/or diameters.

The actuator 48 is activated to displace rectilinearly the upper arm 12 and the lower arm 14 initially as a unit in the first direction D. During the initial stages of the lowering motion the lower arm 14 hangs from the upper arm 12 through abutting contact defined between the lower edge 34L of the tab 34 and the upper surface 12S of the upper arm 12. The tines 14T at the second end 14R of the lower arm 12 guide the lower arm along the operating rod 46.

As best seen in FIG. 2 lowering motion continues until abutting contact occurs between the lower arm 14 and the container 62 to be identified prevents further advance of the lower arm 14. In the construction of the apparatus 10 shown in the Figures, it is the inclined surface 28S of the foot 28 that first makes abutting contact with the container to be identified. Upon abutting contact the actuator 48 continues the displace the upper arm 12 along the axis P. Thus, substantially simultaneously with the occurrence of the abutting contact, relative motion is caused to occur between the upper arm 12 and the lower arm 14.

The motion of the upper arm 12 with respect to the now-stationary lower arm 14 removes the tab 34 (also now-stationary by virtue of its attachment to the alignment post 32) from its interposed position between light emitting element 38E and light receiving element 38R. As the arm 12 advances below the tab 34 the light emitting element 38E and light receiving element 38R are placed in optical communication, thereby generating a signal on the line 38W. Thus, the sensor 38 formed by the combination of the tab 34 and the elements 38E, 38R responds to this relative motion to generate a first signal representative thereof.

The counter 50 responds to the generation of the relative motion signal on the line 38W to generate a signal representative of the magnitude of the vertical displacement undergone by the upper arm 12. This signal, on the line 50W, serves as an address to the memory S. The container identity signal stored in the storage location corresponding to the magnitude of the displacement signal is output on the line 60L from the controller 60.

The abutting contact between the conical surface 28S of the foot 28 and the container 62 draws the container into an operating position in which the axis 62A of the container 62 is collinear with the penetration axis P. The engagement of the container 62 (whether open-mouthed or stoppered) with the foot 28 secures the container in this operating position.

As best seen in FIG. 3 continued displacement of the upper arm 12 by the actuator 48 with respect to the lower arm 14 extends the extraction needle 18 from its initial disposition within the bore 28B. If the container 62 is stoppered the needle 18 is caused to penetrate through the stopper and into the container without the occurrence of bending of the extraction needle 18 because the upper arm 12, the lower arm 14, and the container 62 are colinearly positioned. It is known that the first buckling failure mode of the needle occurs at a much higher force than the frictional force required to overcome insertion of the needle 18 through the stopper. The needle 18 thus enters into the container 62. If the container is of open-mouthed condition no stopper is present and needle 18 enters the container 62 directly.

When the needle 18 contacts the liquid within the container 62 a signal representative of this occurrence is generated by the capacitive level sensor C. The actuator continues to lower the upper arm 12, and thereby the needle 18, for a predetermined distance into the liquid, in accordance with the desired volume of fluid sample to be extracted. Pump M is activated to extract liquid from the container.

After the desired volume of liquid is withdrawn, the actuator 48 is reversed to displace rectilinearly the upper arm 12 in the second direction U (opposed to the first direction D) thereby to withdraw the extraction needle 18 through the stopper and from the container 62. During removal of the extraction needle 18 from the container 62 the weight of the plates 42 together with that of the lower arm 14 is sufficient to generate a holding force (acting on the container 62 in the direction D) that retains the container 62 in the operating position while the extraction needle 18 is withdrawn through the stopper. It lies within the contemplation of the present invention to omit one or both of the plates so long as the weight of the lower arm 14 (with or without a plate or other member thereon) is sufficient to generate the required holding force.

Once the needle 18 is withdrawn from the stopper continued upward motion of the upper arm eventually brings the upper surface 12S thereof into abutting engagement with the lower edge 34L of the tab 34. Thereafter, continued upward motion of the upper arm 12 lifts the lower arm therewith. The motion of the lower arm 14 along the operating rod 46 is again guided by the tines 14T.

Figure 6:
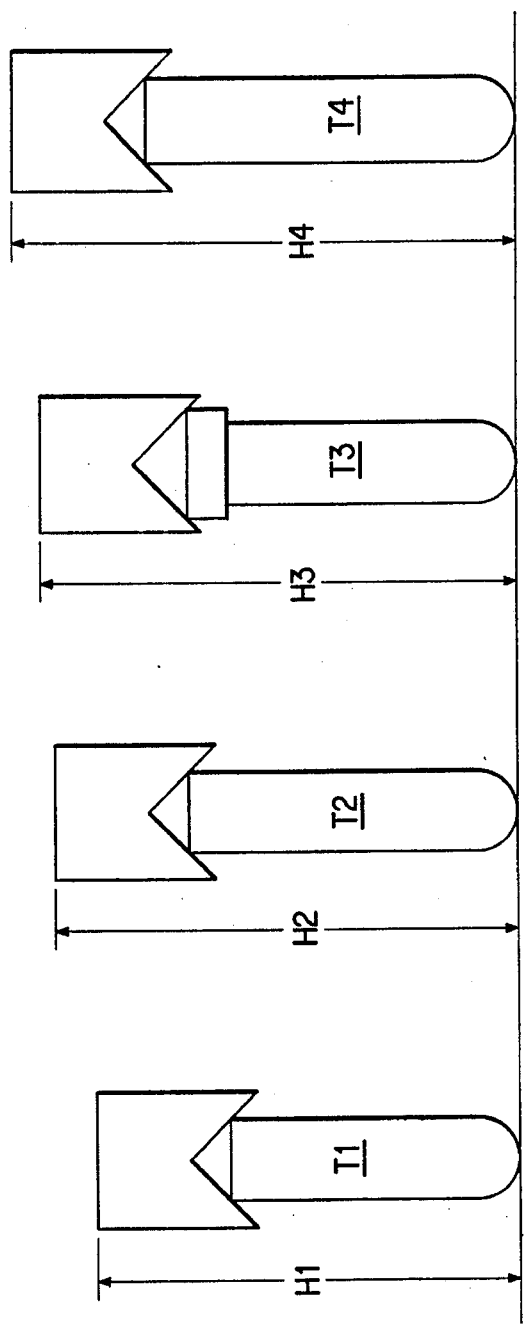

A typical calibration process is illustrated in FIG. 6. The calibration process is usually made at initial setup of the apparatus. In FIG. 6 two stoppered containers T1 and T2 and two open containers T3 and T4 are placed in a known sequence by an operator at the operating position and the apparatus operated as described above to ascertain four different first signals each corresponding to the four different instants in time when the abutting contact between the lower arm 14 and four different containers having types to be identified prevents further advance of the lower arm 14 and simultaneously causes relative motion between the upper arm 12 and lower arm 12 such that sensor 38 responds to the relative motion to generate each of the four different first signals at four different first instants in time. These different first instants in time are each correlated with different displacement signals related to the four different displacements of the upper arm, for example by using a counter in correspondence with the actuator. The displacement signal for each different container is preferably associated with an appropriate range of displacement signals to compensate for minor variations in container and stopper dimensions. Within controller 60 is a memory S having a plurality of storage locations therein, each storage location having an address that corresponds to each different displacement signal, and each storage location is provided by the operator with a container identity signal I determined by the operator to be representative of each of the four different containers. During the calibration process, displacement signals H1 and H2 are thereby correlated with tube types T1 and T2 as being of stoppered type and displacement signals H3 and H4 are thereby correlated with tube types T3 and T4 as being of open-mouthed type. If two ranges of displacement signals partially coincide for containers that are of the same open or same stoppered type, the calibration process remains able to accurately differentiate between open and stoppered containers. In the alternative, if two ranges of displacement signals partially coincide for containers that are not of the same open or same stoppered type, the calibration process is unable to differentiate between open and stoppered containers and one or the other of these particular containers is not employed during operation of the apparatus 10, or a default to assume a stopper is present.

Those skilled in the art, having the benefit of the teachings of the present invention may impart numerous modifications thereto. For example, the invnetion could comprise a second reference datum line such that the bottom end of only open-mouthed containers are supported at the second reference datum line in order to further differentiate between closed and open-mouthed tubes. Such modifications should be construed as lying within the contemplation of the present invention, as defined by the appended claims.

What is claimed is:

1. Apparatus for identifying each of a predetermined plurality of liquid containers, some of which are stoppered and others of which are open-mouthed, the apparatus comprising:

an upper arm and a lower arm, the lower arm being mounted for relative movement along a vertical axis with respect to the upper arm;

an actuator connected to the upper arm for rectilinearly displacing the same;

a sensor responsive to relative motion between the upper and the lower arms to generate a first signal;

means responsive to the first signal for generating a signal representative of the magnitude of the displacement of the upper arm;

means responsive to the magnitude of the displacement signal for generating a container identity signal, the upper and the lower arms being initially displaceable as a unit by the actuator until abutting contact between the lower arm and a container to be identified prevents further advance of the lower arm and substantially simultaneously causes relative motion between the upper and the lower arms such that the sensor responds to the relative motion to generate the first signal.

2. The apparatus of claim 1 further comprising:

a foot attached to the lower arm, the foot having a surface that is inclined with respect to the vertical axis, the inclined surface being that portion of the lower arm which makes abutting contact with the container to be identified.

3. The apparatus of claim 1, wherein each container to be identified has a bottom end thereon, the apparatus further comprising:

a support for supporting the bottom of each of the containers to be identified at the same predetermined reference datum.

4. The apparatus of claim 1 wherein:

the upper arm has an opening therethrough; and the lower arm has an alignment post secured thereto, the alignment post extending from the lower arm and through the opening in the upper arm.

5. The apparatus of claim 4 wherein:

the alignment post has tab extending therefrom, and wherein:

the sensor comprises a light emitting element and a light receiving element disposed in proximity to the opening, the tab being sized to extend between the light emitting element and a light receiving element as the upper and lower arms are moved as unit, relative motion of the lower arm with respect to the upper arm displacing the tab from between the light emitting element and a light receiving element.

6. The apparatus of claim 1 wherein:

an operating rod is connected to the upper arm and to the actuator; and wherein:

the lower arm has a pair of tines formed at an end thereof, the tines bracketing the operating rod to guide the lower arm along the operating rod.

7. The apparatus of claim 1 wherein the means responsive to the second signal for generating a container identity signal comprises:

a memory having a plurality of storage locations therein, each storage location containing a container identity signal representative of one of the plurality of containers, each storage location having an address that corresponds to the magnitude of the displacement signal.

* * * * *